United States Patent
Jung et al.

(10) Patent No.: US 10,004,412 B2
(45) Date of Patent: Jun. 26, 2018

(54) MAGNETOCARDIOGRAPHY ARRANGEMENT AND ERGOMETER FOR SAME

(71) Applicant: BIOMAGNETIK PARK GMBH, Hamburg (DE)

(72) Inventors: Friedrich Jung, Dresden (DE); Hongjoe Jang, Seoul (KR); Jens Schmidt, Garstedt (DE); Dieter Krause, Buchholz (DE)

(73) Assignee: Biomagnetik Park GmbH, Hamburg (DE)

( * ) Notice: Subject to any disclaimer, the term of this patent is extended or adjusted under 35 U.S.C. 154(b) by 814 days.

(21) Appl. No.: 14/367,336

(22) PCT Filed: Dec. 20, 2012

(86) PCT No.: PCT/DE2012/100394
§ 371 (c)(1),
(2) Date: Jun. 20, 2014

(87) PCT Pub. No.: WO2013/091627
PCT Pub. Date: Jun. 27, 2013

(65) Prior Publication Data
US 2015/0038826 A1    Feb. 5, 2015

(30) Foreign Application Priority Data

Dec. 21, 2011  (DE) .................. 10 2011 056 786
Dec. 21, 2011  (DE) .................. 20 2011 052 404 U
(Continued)

(51) Int. Cl.
*A61B 5/04*    (2006.01)
*A61B 5/00*    (2006.01)
(Continued)

(52) U.S. Cl.
CPC ........ *A61B 5/04007* (2013.01); *A61B 5/4884* (2013.01); *A61B 5/04005* (2013.01);
(Continued)

(58) Field of Classification Search
CPC . A61B 5/04005; A61B 5/04007; A61B 6/503; A61B 5/4884; G01R 33/0354; G01R 33/24; G01N 27/82; G01N 27/902
See application file for complete search history.

(56) References Cited

U.S. PATENT DOCUMENTS 5,018,724 A    5/1991  Naser et al.
5,480,366 A *  1/1996  Harnden ............... A63B 69/16
                                                    482/57
(Continued)

FOREIGN PATENT DOCUMENTS

DE    2319301 A1    11/1974
DE    2630025 B1    5/1977
(Continued)

OTHER PUBLICATIONS

English language translation of Korean Office Action dated Jul. 11, 2016, in Korean Application No. 10-2014-7019732.
(Continued)

*Primary Examiner* — Elmer Chao
(74) *Attorney, Agent, or Firm* — Stephan A. Pendorf; Patent Central LLC (57) ABSTRACT

A magnetocardiography arrangement for producing stress magnetocardiograms that comprises a magnetocardiograph (1) and a stress unit (2) consisting of non-magnetic components. The magnetocardiograph (1) and the stress unit (2) are arranged in a shielded chamber (4) for shielding against external magnetic fields, and the stress unit (2) is or includes a bicycle ergometer braked by means of pressurized gas or a pressurized gas mixture from a source (6) for the pressur-
(Continued)

ized gas or the pressurized gas mixture arranged outside the shielded chamber (4).

17 Claims, 4 Drawing Sheets

(30) Foreign Application Priority Data

Dec. 22, 2011 (DE) .................. 10 2011 056 881
Dec. 22, 2011 (DE) .................. 20 2011 052 433 U (51) Int. Cl.
| | |
|---|---|
| G01R 33/24 | (2006.01) |
| G01N 27/90 | (2006.01) |
| G01R 33/035 | (2006.01) |
| A61B 6/00 | (2006.01) |
| G01N 27/82 | (2006.01) |

(52) U.S. Cl.
CPC ........... *A61B 6/503* (2013.01); *A61B 2562/18* (2013.01); *G01N 27/82* (2013.01); *G01N 27/902* (2013.01); *G01R 33/0354* (2013.01); *G01R 33/24* (2013.01)

(56) References Cited

U.S. PATENT DOCUMENTS

| 6,270,445 | B1 | 8/2001 | Dean, Jr. et al. |
| 8,267,842 | B2 | 9/2012 | Schocke et al. |
| 2003/0224911 | A1* | 12/2003 | Warner ................ A63B 21/157 482/57 |
| 2010/0190613 | A1* | 7/2010 | Murray ................ A63B 21/15 482/52 |

FOREIGN PATENT DOCUMENTS

| DE | 9103737 U1 | 6/1991 |
| DE | 3486014 T2 | 5/1993 |
| DE | 102006056282 A1 | 6/2008 |
| EP | 0371156 A1 | 6/1990 |
| EP | 0379227 A2 | 7/1990 |
| EP | 1714615 A1 | 10/2006 |
| WO | 2006111385 A1 | 10/2006 |

OTHER PUBLICATIONS

Lee, Ha-Na "A study on External Magnetic Noise Reduction in Magnetocardiography" Kyung Hee University, a masters thesis (Feb. 2004), Korea.

Dania Di Pietro Paolo "Numerical Methods for improved signal to noise ratios in spatiotemporal biomedical data (Dissertation)", Aug. 4, 2010 (Aug. 4, 2010), pp. FP, i-xii, 1-138, XP002695420, DB Thueringen, Germany, retrieved from the internet: URL:http://www.db-thueringen.de/servlets/DocumentServlet?id=16261 (retrieved on Apr. 15, 2013), p. 22, lines 8-18, figure 2.8.

Quistorff B et al.: "A Simple Calf Muscle Ergometer For Use In A Standard Whole Body MR Scanner", Magnetic Resonance In Medicine, vol. 13, No. 3, Mar. 1, 1990 (Mar. 1, 1990), pp. 444-449, XP000132474, Academic Press, Duluth, MN, US ISSN: 0740-3194, p. 444, line 10-p. 447, line 25; figures 1, 2.

International Search Report in International Application No. PCT/DE2012/100394, dated May 15, 2013.

Dania Di Pietro Paolo "Numerical Methods for improved signal to noise ratios in spatiotemporal biomedical data (Dissertation)", Aug. 4, 2010) Aug. 4, 2010, pp. FP, i-xii, 1-138, XP002695420, DB Thueringen, Germany, retrieved from the internet: URL:http://www.db-thueringen.de/servlets/DocumentServlet?id=16261 (retrieved on Apr. 15, 2013), p. 22, lines 8-18, figure 2.8.

Quistorff B et al.: "A Simple Calf Muscle Ergometer for Use in a Standard Whole-Body MR Scanner", Magnetic Resonance in Medicine, vol. 13, No. 3, Mar. 1, 1990 (Mar. 1, 1990), pp. 444-449, XP000132474, Academic Press, Duluth, MN, US ISSN: 0740-3194, p. 444, line 10-p. 447, line 25; figures 1, 2.

English language International Preliminary Report on Patentability dated Jun. 24, 2014, in International Application No. PCT/DE2012/100394.

\* cited by examiner

MAGNETOCARDIOGRAPHY ARRANGEMENT AND ERGOMETER FOR SAME

The invention relates to a magnetocardiography arrangement and an ergometer for same.

Magnetocardiography is a method in which the magnetic activity of the heart is recorded contactlessly. In order to measure the extremely weak magnetic field generated by the human heart, highly sensitive detectors made of superconducting quantum interferometers, or what are known as SQUIDs, are used.

With the aid of magnetocardiography, stress magnetocardiograms are produced to determine heart defects, for example a coronary heart disease. Here, the heart is stressed generally pharmacologically by injection of a suitable agent, for example adenosine or dobutamine. It is also known to stress the heart by means of an ergometer.

By way of example, a magnetocardiography arrangement is known from EP 03711156 A1, with which a flywheel-based bicycle ergometer consisting of non-magnetic structural elements is used. In addition, a magnetocardiography arrangement is known from DE 10 2006 056 282 A1, with which a non-magnetic bicycle ergometer is likewise used, but this time based on hydraulics.

The object of the present invention is to provide an improved magnetocardiography arrangement for producing stress magnetocardiograms.

This object is achieved by the subject matter of claim 1. Expedient embodiments of the invention are specified in the dependent claims.

To achieve the object, the invention provides a magnetocardiography arrangement for producing stress magnetocardiograms, which comprises a magnetocardiograph and a stress unit consisting of non-magnetic components, wherein the magnetocardiograph and the stress unit are arranged in a shielded chamber for shielding against external magnetic fields, and wherein the stress unit is or comprises a bicycle ergometer braked by means of pressurised gas or a pressurised gas mixture from a source for the pressurised gas or the pressurised gas mixture arranged outside the shielded chamber.

The magnetocardiography arrangement according to the invention comprises a stress unit, which is based on an ergometer consisting of non-magnetic materials and braked by means of pressurised gas or a pressurised gas mixture, preferably pneumatically. A suitably formed ergometer is described further below. The use of a compression gas brake, for example a pneumatic brake, has the advantage that the corresponding components in the shielded chamber can be produced completely from non-magnetic materials, for example lines made of copper or plastic, in a relatively unproblematic manner. Problems with a potential escape of hydraulic fluid are likewise avoided. Since the compression gas source, for example the compressed air source, is arranged outside the shielded chamber, a further cause of interference for the sensitive measurement is avoided. In addition, it is advantageous in the case of the use of compressed air for the stress unit to be connectable to the central compressed air supply often usual in clinics.

Here, an "ergometer" is understood to mean a device with the aid of which a person can be subjected to a defined physical stress. Here, a bicycle ergometer is understood to mean an ergometer in which a crank is moved by the person against a resistance, for example by means of pedals, in a circular rotational movement, for example. Here, the rotational movement may be generated by movement of the legs and/or the arms. The term "non-magnetic" means that the materials have no or no significant magnetic field interfering with the measurement by the SQUID, and in particular are non-ferromagnetic. Examples of such materials are ceramics, such as zirconium oxide ($ZrO_2$), silicon nitride ($SiN_4$), plastics such as polyoxymethylene (POM), polytetrafluoroethylene (PTFE) or polyether ether ketone (PEEK), or metals such as aluminium or copper. A "pressurised gas" or a "pressurised gas mixture" is understood to means any gas or any gas mixture to which pressure is applied. The expression "compression gas" used here is synonymous with the expressions "pressurised gas" and "pressurised gas mixture" and includes both terms. The gas(es) may be, for example, air, nitrogen, helium, oxygen or any gas mixtures, for example a nitrogen/oxygen mixture. The gas(es) may be a gas or a gas mixture that is liquefied under pressure and/or with cooling, for example liquid nitrogen. The gas(es) is/are preferably compressed air, that is to say compressed ambient air. The pressure, for example, may be 5 bar, but possibly also lower or higher. The terms "source for a pressurised gas", "source for a pressurised gas mixture" or "compression gas source" are understood to mean the point from which the pressurised gas originates or is held before it is conveyed, where applicable, via suitable lines. For example, the source may be one or more compressors and/or compressed gas bottles. A "magnetocardiograph" is understood to mean a device for measuring cardio magnetic fields. A cardio magnetic field is a bio magnetic field that is produced by the electrical activity or interaction of heart cells, for example in the human body. Cardio magnetic fields are comparatively weak and for example lie in the region of a few tens of picoteslas (1 pT=$10^{-12}$ T).

The stress unit is preferably arranged on a patient bed consisting of non-magnetic components, but can also be provided separately.

The magnetocardiograph and the stress unit are particularly preferably arranged in a shielded chamber for shielding against external magnetic fields, and the stress unit is connected by means of non-magnetic lines to a pressure regulation unit preferably arranged within the shielded chamber. The pressure regulation unit is connected to the source, arranged outside the shielded chamber, for a pressurised gas or a pressurised gas mixture, for example a compressed gas source. The compressed gas source may be the central compressed air supply of a clinic.

The magnetocardiograph and/or the pressure regulation unit are preferably connected to an operating and control unit arranged outside the shielded chamber. The resistance for the stress unit set or settable by means of the pressure regulation unit can particularly preferably be measured and/or regulated via the operating and control unit. The stress unit and therefore the patient can thus be subjected to a predefined stress, and the stress applied can be measured and recorded where applicable. The operating and control unit may be a personal computer set up in a suitable manner.

It is also preferred to record an electrocardiogram (ECG) parallel to the magnetocardiogram (MCG) and to provide an ECG device positioned outside the shielded chamber for this purpose, the ECG device having ECG electrode plugs and leads consisting of non-magnetic components, reaching into the shielded chamber and connectable to the patient.

In order to facilitate patient monitoring, a monitoring camera is preferably provided in the shielded chamber in a magnetically shielded housing, the signals of said monitoring camera being conveyed via shielded cables from the shielded chamber and preferably to the operating and control unit.

The invention also provides an ergometer that is well suited for use in the production of stress magnetocardiograms and that can be used advantageously as a stress unit in the magnetocardiography arrangement according to the invention. The ergometer according to the invention consists of non-magnetic material and comprises a flywheel mass, which can be rotated by means of hand or foot actuation via a transmission having a gear ratio of at least 1:10.

In the case of the ergometer, which is preferably a bicycle ergometer, a flywheel mass is rotated via a transmission. Here, the transmission preferably has at least two stages. Since the flywheel mass is driven by a transmission having a high gear ratio of at least 1:10, a particularly uniform operation that is also comfortable for example for ill patients is made possible. For patients suffering for example from heart disease, it is often difficult or even impossible to overcome a resistance which deviates significantly over the angle of rotation and which is opposed by the brake of the drive movement. Due to the comparatively high speed of rotation of the flywheel mass achieved by means of the high gear ratio, a higher energy storage capacity can be achieved with constant installation space, even with the often low density of non-magnetic materials. A high energy storage capacity in turn enables a uniform pedalling motion. The invention makes it possible to increase the energy storage capacity of the ergometer to such an extent that it is easily possible to overcome the dead centres of the drive, for example of the crank drive, even if the ergometer is braked. A moderate and selective stressing of patients is thus possible, for example so as to produce a magnetocardiogram under stress.

The gear ratio is preferably 1:10 to 1:20, more preferably 1:10 to 1:18, more preferably 1:10 to 1:15 and particularly preferably 1:10 to 1:13, for example approximately 1:12. Intermediate values of the above range, for example 1:11, 1:12.25 and other ratios are also disclosed here expressly.

In a preferred embodiment the ergometer further comprises a brake unit actuatable by means of pressurised gas or a pressurised gas mixture for braking the rotation of the flywheel mass. Here, the braking force of the brake unit can be set preferably by means of the pressurised gas or by the pressurised gas mixture. The pressurised gas or the pressurised gas mixture may be compressed air, nitrogen, oxygen, helium, oxygen or mixtures thereof. The pneumatic setting of the braking force of the brake unit is preferably implemented by means of compressed air. The use of a compression gas brake, for example a pneumatic brake, has the advantage that the corresponding components, for example lines, in the shielded chamber can be produced from non-magnetic materials, such as copper or plastic. In addition, it is advantageous, for example in the case of the use of compressed air, that the ergometer can be connected to the central compressed air supply often conventional in clinics. A continuously adjustable braking force of the brake unit is advantageously adjustable via a suitable controller, such that a defined braking torque for the stressing of the patient can be set.

The brake unit is preferably a pneumatic cylinder, in which a piston is movably arranged, which for example can be engaged with a brake disc, preferably in a force-locked manner, such that the braking force generated by the brake unit can be set via the air pressure. The braking force of the brake unit is preferably set via a pressure controller. A defined and preferably continuously variable braking effect can be set by means of this pressure controller.

In a preferred embodiment of the ergometer, it comprises a two-stage transmission, which consists of four shafts, wherein two shafts are formed as hollow shafts, which are each arranged coaxially with one of the two other shafts preferably formed as solid shafts. In an embodiment as a bicycle ergometer, pedal arms are preferably mounted on the first shaft preferably formed as a solid shaft, the first shaft being rotatable by pedalling motions via said pedal arms. The rotational movement is transmitted via a first gear stage from the first shaft to the second shaft, likewise formed as a solid shaft, and the speed of rotation is altered. The rotational movement is transmitted via the second gear stage from the third shaft formed as a hollow shaft to the fourth shaft, likewise formed as a hollow shaft, and the speed of rotation is altered. The flywheel mass is connected to the fourth shaft in a form-fitting or force-locked manner. In this embodiment, the ergometer according to the invention is particularly compact, such that it can be integrated more easily into a bed, for example.

In a particularly preferred embodiment a freewheel clutch is arranged between the first and second gear stage. To this end, the freewheel clutch can be arranged for example between the second shaft and the hollow shaft mounted thereon. The integration of a freewheel clutch is particularly advantageous so as to prevent a further rotation of the pedal cranks or the pedal arms in the case of a bicycle ergometer when the person using the ergometer pedals more slowly or stops pedalling. In particular with older and/or weak individuals, this is advantageous for safety reasons.

For example, the transmission may be a gear train or a belt drive. In a preferred embodiment the transmission is constituted by belt drives. In the case of a belt drive, a first belt pulley is preferably arranged on the first shaft, a second belt pulley is preferably arranged on the second shaft, a third belt pulley is preferably arranged on the third shaft, and a fourth belt pulley is preferably arranged on the fourth shaft, wherein the first and second belt pulley and the third and fourth belt pulley are connected in each case via a belt.

In a preferred embodiment of the ergometer, a brake disc is connected to the fourth shaft, formed as a hollow shaft, in a form-fitting or force-locked manner and can be engaged with a pneumatic cylinder of the brake unit. Effective braking of the rotation of the flywheel mass is thus made possible. The brake disc and/or the piston of the pneumatic cylinder have/has a suitable brake lining.

The invention will be explained in greater detail hereinafter on the basis of the accompanying figures, purely for illustrative purposes, in which.

Figure 1:
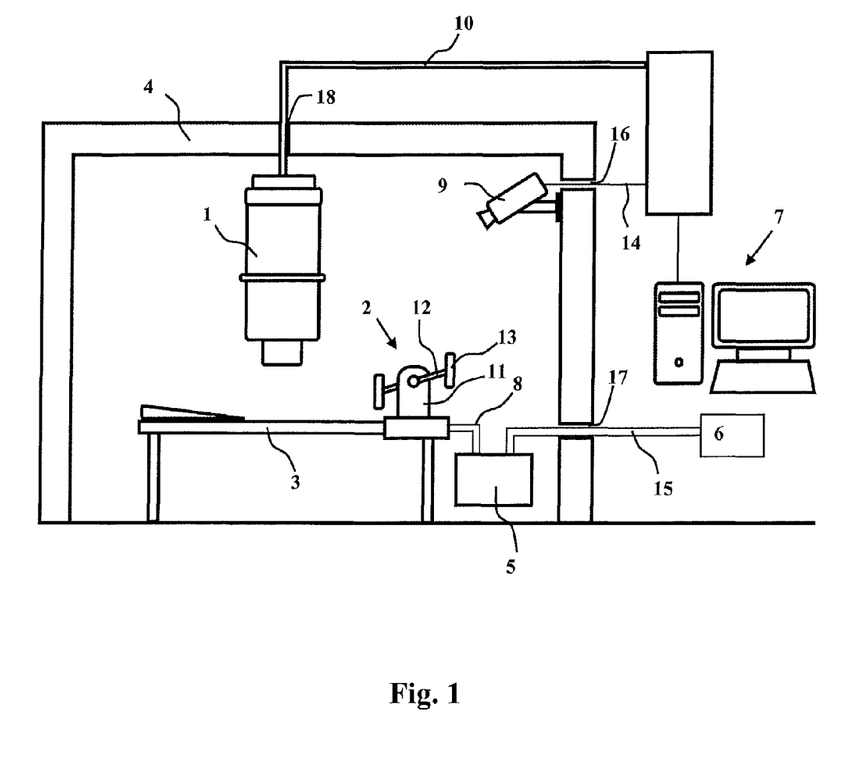
FIG. 1 shows a schematic view of a magnetocardiography arrangement according to the invention.

FIG. 1 shows a magnetocardiography arrangement according to the invention. What is shown is a magnetocardiograph 1 above a patient bed 3, at the foot end of which a stress unit 2 formed as a bicycle ergometer is provided. The magnetocardiograph 1 and the patient bed 3 with the stress unit 2 are located in a shielded chamber 4, of which the interior is shielded from external electromagnetic interferences.

The patient bed 3 and stress unit 2 are manufactured completely from non-ferromagnetic materials, such as aluminium and suitable plastics. The magnetocardiograph 1 or the sensor units thereof are connected via suitable supply and signal lines 10 to the operating and control unit 7 outside the shielded chamber 4.

To record a stress magnetocardiogram, a bicycle ergometer 2 is arranged at the foot end of the patient bed 3 so as to be displaceable in the longitudinal direction of the patient bed 3. The bicycle ergometer 2 comprises pedal arms 12, mounted rotatably in a housing 11, with pedals 13. Lines 8 for compressed air are provided in the housing 11 and are connected to a pressure regulation unit 5. Further lines 15 are connected to a compressed air source 6 arranged outside the shielded chamber 4. Instead of compressed air, a liquefied gas, for example nitrogen gas, can also be stored in a pressurised container, for example. At room temperature, a corresponding pressure builds up. In this case, the pressure regulation unit 5 can also be fitted on the pressure container, and the lines 8 can be connected directly to the pressure regulation unit 5.

All parts of the bicycle ergometer 2 and the lines 8, which are arranged within the shielded chamber 4, are produced from non-ferromagnetic materials.

To monitor the patient (not illustrated here) resting on the patient bed 3, a monitoring camera 9 housed in a magnetically shielded housing is mounted in the shielded chamber 4. The camera image is transmitted via a signal line 14 guided out from the shielded chamber 4 to the operating and control unit 7 or to a separate monitor (not illustrated).

All supply or connection lines are introduced into the shielded chamber 4 via corresponding bushings 16, 17, 18.

Figure 2:
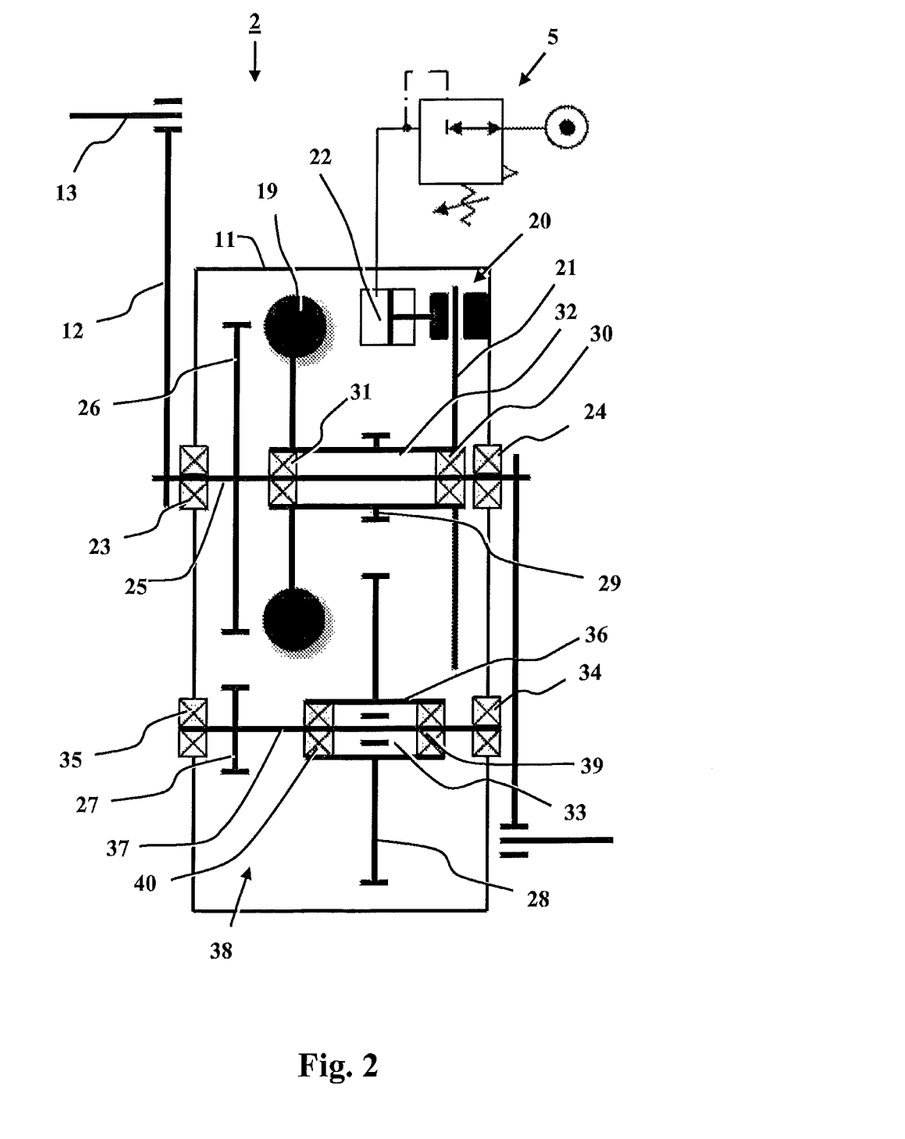
FIG. 2 shows a schematic diagram of an ergometer according to the invention.

FIG. 2 schematically shows an embodiment of an ergometer according to the invention, as can be used advantageously as a stress unit 2 in the magnetocardiography arrangement illustrated in FIG. 1. The ergometer 2 is formed as a bicycle ergometer and is manufactured largely from polyoxymethylene (POM) and one or more other non-ferromagnetic plastics/metals/ceramics. A flywheel mass 19 is arranged in a housing 11 and is manufactured for example from POM or aluminium and can be rotated via a two-stage transmission 38. To this end, two shafts 25 and 37 arranged parallel to one another are mounted rotatably in the housing 11 by means of bearings 23, 24 and 34, 35. The first shaft 25 formed here as a solid shaft is guided outwardly via openings in the housing 11. There, pedal arms 12 with pedals 13 are mounted on the shaft 25. With the aid of the pedal arms 12 and pedals 13, the shaft 25 can be rotated. A belt pulley 26 is fixed on the shaft 25 inside the housing 11 and is rotated with the shaft 25. A belt pulley 27 on the second shaft 37, which is likewise formed as a solid shaft, is associated with the belt pulley 26 on the shaft 25. When the first shaft 25 is rotated, the second shaft 37 is also rotated via a belt (not illustrated here) guided over the peripheral faces of the belt pulleys 26, 27. The belt pulley 26 has a larger diameter than the belt pulley 27, such that a corresponding first gear ratio results. A third shaft 36 formed as a hollow shaft is rotatably mounted externally on the shaft, coaxially with the shaft 37, by means of bearings 39, 40, a freewheel clutch 33 being arranged in said third shaft. A belt pulley 28 is fastened on the hollow shaft 36. The freewheel clutch 33 is designed such that the hollow shaft 36 and the belt pulley 28 rotate with the shaft 37 in the provided direction of rotation, with a decoupling of the hollow shaft 36 from the shaft 37 with rotation in the opposite direction or with slower rotation of the shaft 37 with respect to the hollow shaft 36. A belt pulley 29 is associated with the belt pulley 28 and is mounted on a fourth shaft 32, likewise formed as a hollow shaft, which is mounted by means of bearings 30, 31 on the shaft 25. A belt (not illustrated here) placed around the peripheral faces of the belt pulleys 28, 29 transmits the rotational movement of the hollow shaft 36 to the hollow shaft 32. Here, the belt pulley 28 has a larger diameter than the belt pulley 29, such that a corresponding second gear ratio results. The respective gear ratios can be set via the ratios of the diameters of the belt pulleys 26, 27, 28 and 29 to one another and can be matched to the respective requirements. On the whole, a gear ratio of at least 1:10, for example of 12.25, is provided between the first shaft 25 and the fourth shaft 32. A flywheel mass 19, which is disc-shaped for example, is fastened on the hollow shaft 32 and rotates with the hollow shaft 32. A brake disc 21 is also fastened on the hollow shaft 32 and can be brought into engagement with a pneumatic cylinder 22 such that the friction between the brake disc 21 and the pneumatic cylinder 22 opposes the rotational movement of the hollow shaft 32 and therefore of the flywheel mass 19 by a corresponding resistance. The contact pressure of the pneumatic cylinder 22 on the brake disc 21 and therefore the resistance against the rotational movement of the flywheel mass 19 can be adjusted preferably continuously by means of a pressure regulation unit 5.

When the ergometer 2 is actuated in the correct direction, for example by forwards pedalling motions of a patient, the shaft 25 is initially rotated with the belt pulley 26 located thereon via the pedal arms 12. This rotational movement is transmitted with a first gear ratio via a belt between the belt pulley 26 and the belt pulley 27 to the shaft 37 mounted rotatably in the housing 11 parallel to the shaft 25. The freewheel clutch 33 engages the hollow shaft 36 with the shaft 37, such that the hollow shaft 36 rotates with the shaft 37. The belt pulley 28 likewise rotated in this way transmits the rotational movement via a belt, which connects the belt pulley 28 to the belt pulley 29, with a second gear ratio to the hollow shaft 32 mounted rotatably on the shaft 25. The flywheel mass 19 arranged on the hollow shaft 32 is thus rotated. If the rotational movement of the shaft 25 and therefore of the shaft 37 slows or if the rotational movement stops entirely, for example because the patient pedals more slowly or stops pedalling entirely, the freewheel clutch 33 arranged between the first and second gear stage ensures that the pedal arms 12 do not rotate further, whereas the flywheel mass 19 continues its rotational movement about the shaft 25, provided it is not braked or stopped by the pneumatic cylinder 22 acting on the brake disc 21.

Figure 3:
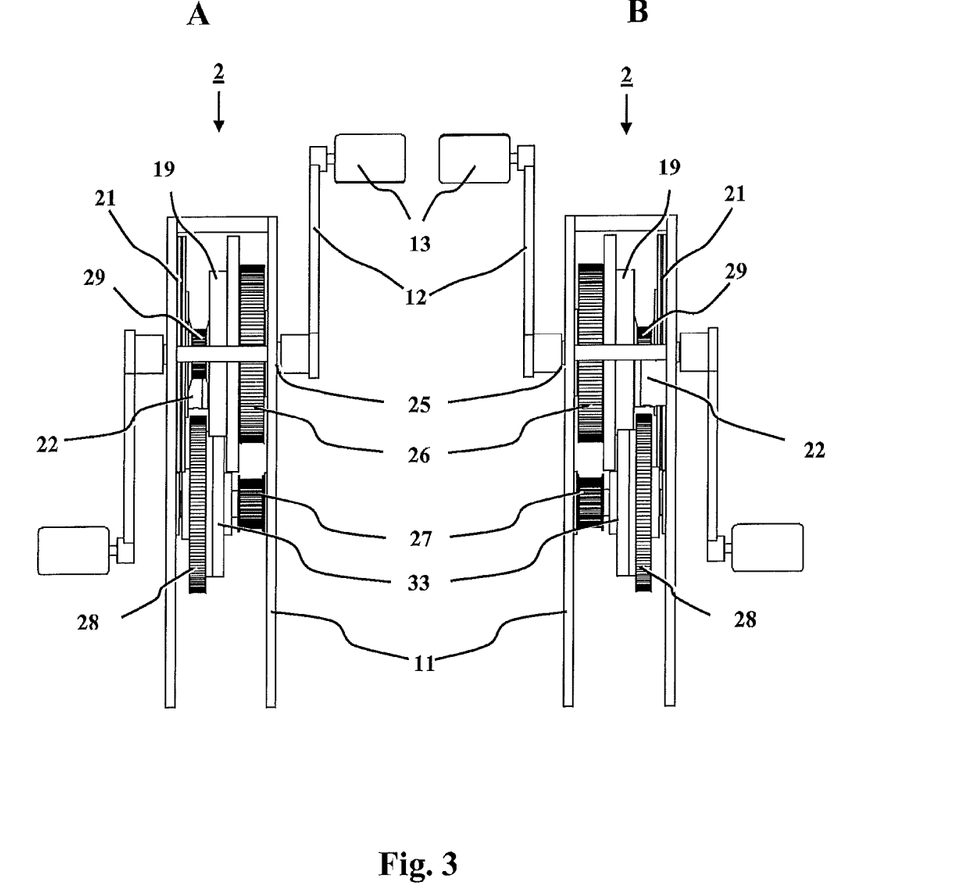
FIG. 3 shows an illustration of an embodiment of an ergometer according to the invention in a front view (A) and rear view (B)
Figure 4:
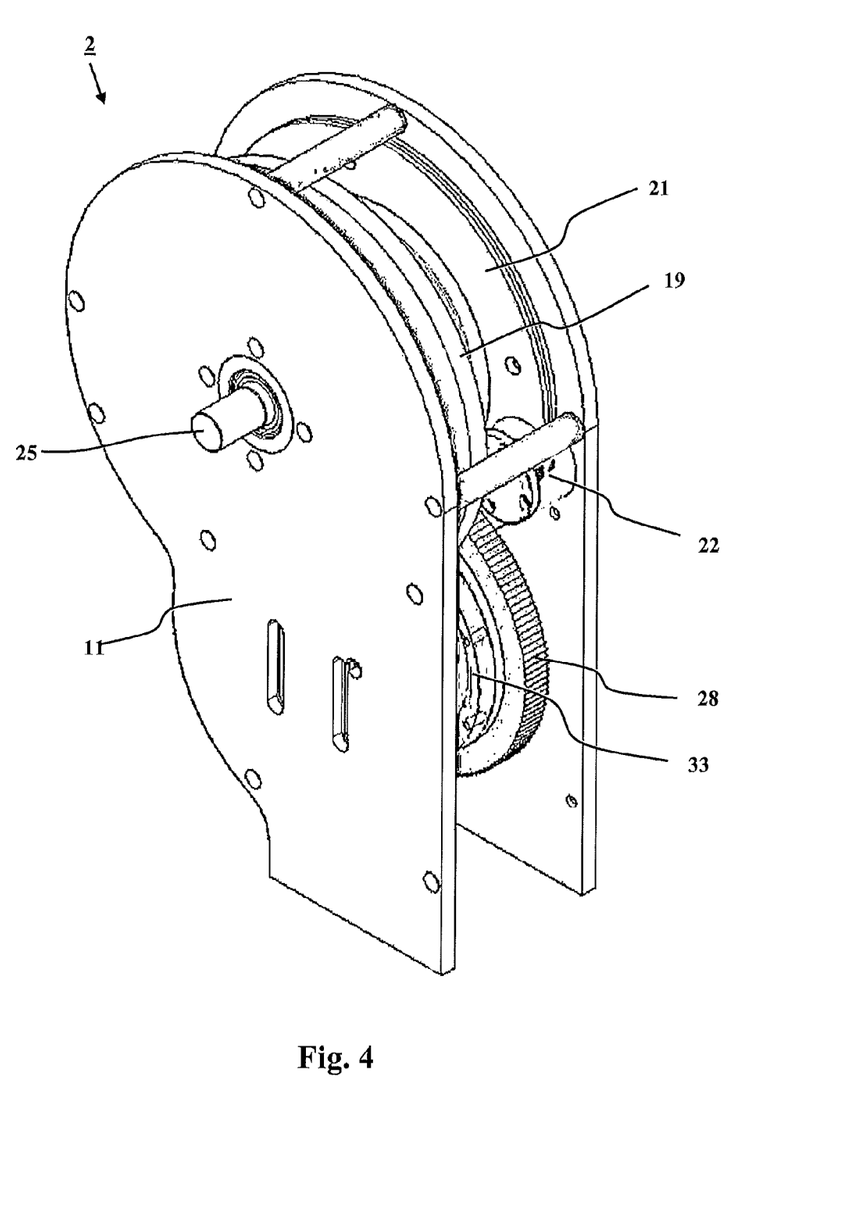
FIG. 4 shows an isometric view of the ergometer from FIG. 3.

FIGS. 3 and 4 show views of an embodiment of the ergometer according to the invention. FIG. 3A shows a front view, FIG. 3B shows a rear view, and FIG. 4 shows an isometric view, wherein part of the housing 11 has been removed in each case. In order to avoid repetitions, reference is made to FIG. 2 for a description of the function and interaction of the individual ergometer components. Here, it is additionally conceivable for the belt pulleys 26, 27, 28, 29 to be formed preferably as toothed pulleys. In addition, it can be seen that the flywheel mass 19 is disc-shaped. The ergometer has a very compact arrangement of the individual components.

LIST OF REFERENCE SIGNS 1 magnetocardiograph
2 stress unit
3 patient bed
4 shielded chamber
5 pressure regulation unit
6 source for a pressurised gas or a pressurised gas mixture
7 operating and control unit
8 lines 9 monitoring camera
10 supply and signal lines
11 housing
12 pedal arm
13 pedals
14 signal line
15 lines
16 bushing
17 bushing
18 bushing
19 flywheel mass
20 brake unit
21 brake disc
22 pneumatic cylinder
23 bearing
24 bearing
25 shaft
26 belt pulley
27 belt pulley
28 belt pulley
29 belt pulley
30 bearing
31 bearing
32 shaft
33 freewheel clutch
34 bearing
35 bearing
36 shaft
37 shaft
38 transmission
39 bearing
40 bearing

The invention claimed is:

1. A magnetocardiography arrangement for producing stress magnetocardiograms, comprising
a magnetocardiograph (1) and
a stress unit (2) consisting of non-magnetic components, wherein the magnetocardiograph (1) and the stress unit (2) are arranged in a shielded chamber (4) for shielding against external magnetic fields, and
wherein the stress unit (2) is or comprises a bicycle ergometer braked by means of pressurised gas or a pressurised gas mixture from a source (6) for the pressurised gas or the pressurised gas mixture arranged outside the shielded chamber (4), and wherein the stress unit (2) comprises a flywheel mass (19) rotatable by means of hand or foot actuation via a transmission (38) with a gear ratio of at least 1:10 and a brake unit (20) actuatable by means of the pressurised gas or the pressurised gas mixture for braking the rotation of the flywheel mass (19), wherein the braking force of the brake unit (20) can be set by means of the pressurised gas or the pressurised gas mixture, and
wherein the stress unit (2) is connected by means of non-magnetic lines (8) to a pressure regulation unit (5) arranged within the shielded chamber (4) and the pressure regulation unit (5) is connected to the source (6), arranged outside the shielded chamber (4), for the pressurised gas or the pressurised gas mixture.

2. The magnetocardiography arrangement according to claim 1, wherein the pressurised gas or the pressurised gas mixture is compressed air, nitrogen, oxygen, helium, oxygen or mixtures thereof.

3. The magnetocardiography arrangement according to claim 1, wherein the flywheel mass (19) is rotatable by means of hand or foot actuation via a transmission (38) with a gear ratio of from 1:10 to 1:20.

4. The magnetocardiography arrangement according to claim 3, wherein the transmission (38) of the stress unit (2) is a two stage transmission and comprises four shafts (25, 37, 36, 32), of which the third and fourth shaft (36, 32) are each formed as hollow shafts, and wherein the fourth shaft (32) is rotatably mounted coaxially on the first shaft (25), and the third shaft (36) is rotatably mounted coaxially on the second shaft (37), the flywheel mass (19) is fastened on the fourth shaft (32), and wherein the shafts (25, 37, 36, 32) are brought into engagement in such a way that a rotational movement of the first shaft (25) is transmitted with a first gear ratio to the second shaft (37), from this to the third shaft (36) and from this with a second gear ratio to the fourth shaft (32).

5. The magnetocardiography arrangement according to claim 4, wherein a freewheel clutch (33) is arranged between the second shaft (37) and the third shaft (36).

6. The magnetocardiography arrangement according to claim 4, wherein the transmission (38) is a belt drive.

7. The magnetocardiography arrangement according to claim 6, wherein a first belt pulley (26) is arranged on the first shaft (25), a second belt pulley (27) is arranged on the second shaft (37), a third belt pulley (28) is arranged on the third shaft (36), a fourth belt pulley (29) is arranged on the fourth shaft (32), and wherein the first and second belt pulley (26, 27) and also the third and fourth belt pulley (28, 29) are connected in each case via a belt.

8. The magnetocardiography arrangement according to claim 4, wherein the brake unit (20) comprises a pneumatic cylinder (22), which can be brought into engagement with a brake disc (21) fastened on the fourth shaft (32).

9. The magnetocardiography arrangement according to claim 3, wherein the flywheel mass (19) is rotatable by means of hand or foot actuation via a transmission (38) with a gear ratio of from 1:10 to 1:18.

10. The magnetocardiography arrangement according to claim 3, wherein the flywheel mass (19) is rotatable by means of hand or foot actuation via a transmission (38) with a gear ratio of from 1:10 to 1:15.

11. The magnetocardiography arrangement according to claim 3, wherein the flywheel mass (19) is rotatable by means of hand or foot actuation via a transmission (38) with a gear ratio of from 1:10 to 1:13.

12. The magnetocardiography arrangement according to claim 1, wherein the pressurised gas or the pressurised gas mixture is compressed air.

13. The magnetocardiography arrangement according to claim 1, wherein the stress unit (2) is arranged on a patient bed (3) consisting of non-magnetic components.

14. The magnetocardiography arrangement according to claim 1, wherein the pressurised gas mixture is a compressed air source.

15. The A magnetocardiography arrangement for producing stress magnetocardiograms, comprising
a magnetocardiograph (1) and
a stress unit (2) consisting of non-magnetic components, wherein the magnetocardiograph (1) and the stress unit (2) are arranged in a shielded chamber (4) for shielding against external magnetic fields, and
wherein the stress unit (2) is or comprises a bicycle ergometer braked by means of pressurised gas or a pressurised gas mixture from a source (6) for the pressurised gas or the pressurised gas mixture arranged outside the shielded chamber (4), and wherein the stress unit (2) comprises a flywheel mass (19) rotatable by means of hand or foot actuation via a transmission (38) with a gear ratio of at least 1:10 and a brake unit (20) actuatable by means of the pressurised gas or the pressurised gas mixture for braking the rotation of the flywheel mass (19), wherein the braking force of the brake unit (20) can be set by means of the pressurised gas or the pressurised gas mixture, wherein the stress unit (2) is connected by means of non-magnetic lines (8) to a pressure regulation unit (5) arranged within the shielded chamber (4) and the pressure regulation unit (5) is connected to the source (6), arranged outside the shielded chamber (4), for the pressurised gas or the pressurised gas mixture, and wherein the pressure regulation unit (5) is connected to an operating and control unit (7) arranged outside the shielded chamber (4).

16. The magnetocardiography arrangement according to claim 15, wherein the resistance for the stress unit (2) set by means of the pressure regulation unit (5) can be measured and/or regulated via the operating and control unit (7).

17. A magnetocardiography arrangement for producing stress magnetocardiograms, comprising a magnetocardiograph (1) and a stress unit (2) consisting of non-magnetic components, wherein the magnetocardiograph (1) and the stress unit (2) are arranged in a shielded chamber (4) for shielding against external magnetic fields, and wherein the stress unit (2) is or comprises a bicycle ergometer braked by means of pressurised gas or a pressurised gas mixture from a source (6) for the pressurised gas or the pressurised gas mixture arranged outside the shielded chamber (4), and wherein the stress unit (2) comprises a flywheel mass (19) rotatable by means of hand or foot actuation via a transmission (38) with a gear ratio of at least 1:10 and a brake unit (20) actuatable by means of the pressurised gas or the pressurised gas mixture for braking the rotation of the flywheel mass (19), wherein the braking force of the brake unit (20) can be set by means of the pressurised gas or the pressurised gas mixture, wherein the stress unit (2) is connected by means of non-magnetic lines (8) to a pressure regulation unit (5) arranged within the shielded chamber (4) and the pressure regulation unit (5) is connected to the source (6), arranged outside the shielded chamber (4), for the pressurised gas or the pressurised gas mixture, and wherein to record an ECG in parallel, an ECG device positioned outside the shielded chamber (4) is provided and consists of non-magnetic components and has ECG electrode plugs and leads, reaching into the shielded chamber (4) and connectable to the patient.

* * * * *